United States Patent
Li et al.

(10) Patent No.: US 11,819,610 B2
(45) Date of Patent: *Nov. 21, 2023

(54) VISUAL LARYNGEAL MASK

(71) Applicant: Zhejiang UE Medical Corp., ZheJiang (CN)

(72) Inventors: Hongbo Li, ZheJiang (CN);
Mingzhang Zuo, ZheJiang (CN);
Ziqing Hei, ZheJiang (CN); Shanglong Yao, ZheJiang (CN); Xuerui Xiong, ZheJiang (CN); Weiping Li, ZheJiang (CN); Weidong Wang, ZheJiang (CN);
Taohong Wang, ZheJiang (CN);
Mengya Huang, ZheJiang (CN);
Jinmin Cai, ZheJiang (CN)

(73) Assignee: Zhejiang UE Medical Corp., ZheJiang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/960,832

(22) Filed: Oct. 6, 2022

(65) Prior Publication Data
US 2023/0033504 A1  Feb. 2, 2023

Related U.S. Application Data

(63) Continuation of application No. 16/467,039, filed as application No. PCT/CN2018/113157 on Oct. 31, 2018, now Pat. No. 11,517,693.

(30) Foreign Application Priority Data

Feb. 7, 2018 (CN) .......................... 201810124111.1
Jul. 10, 2018 (CN) .......................... 201821088839.5

(51) Int. Cl.
*A61M 16/04* (2006.01)
*A61B 1/06* (2006.01)
(Continued)

(52) U.S. Cl.
CPC ..... *A61M 16/0434* (2013.01); *A61B 1/00082* (2013.01); *A61B 1/00091* (2013.01);
(Continued)

(58) Field of Classification Search
CPC .. A61M 16/00; A61M 16/04; A61M 16/0402; A61M 16/0409; A61M 16/0415;
(Continued)

(56) References Cited

U.S. PATENT DOCUMENTS 6,003,514 A * 12/1999 Pagan ................... A61M 16/04
128/200.26
6,240,922 B1 * 6/2001 Pagan ................... A61M 16/04
128/207.14
(Continued)

FOREIGN PATENT DOCUMENTS

CN  106178209 A * 12/2016
CN  206167560 U * 5/2017

*Primary Examiner* — Colin W Stuart
(74) *Attorney, Agent, or Firm* — JCIP GLOBAL INC.

(57) ABSTRACT

The present invention provides an improved visual laryngeal mask comprising a tube, an end of the tube is provided with a fixing seat. The fixing seat is provided with an airbag, and the fixing seat has a recess which is provided with an airway opening. An imaging cavity extends longitudinally inside an inner wall of the tube. The imaging cavity has a built-in imaging device, and the imaging cavity protrudes forward relative to the airway opening to form a stopper which prevents an epiglottis from blocking the imaging device. A front end of the stopper is concaved to form a recess, and an opening of the imaging cavity is located at a low point of the recess.

9 Claims, 10 Drawing Sheets

(51) Int. Cl.
*A61B 1/12* (2006.01)
*A61B 1/267* (2006.01)
*A61B 1/00* (2006.01)

(52) U.S. Cl.
CPC ............ *A61B 1/0661* (2013.01); *A61B 1/126* (2013.01); *A61B 1/267* (2013.01); *A61M 16/047* (2013.01); *A61M 16/0409* (2014.02); *A61M 16/0463* (2013.01)

(58) Field of Classification Search
CPC .......... A61M 16/0429; A61M 16/0434; A61M 16/0463; A61M 2210/065; A61M 2210/0656; A61M 2210/1025; A61M 2210/1028; A61B 1/0661; A61B 1/126; A61B 1/267; A61B 1/00091; A61B 1/00082
See application file for complete search history.

(56) References Cited

U.S. PATENT DOCUMENTS

| | | | |
|---|---|---|---|
| 11,517,693 B2 * | 12/2022 | Zuo | A61B 1/267 |
| 2006/0162730 A1 * | 7/2006 | Glassenberg | A61M 16/04 |
| | | | 128/207.14 |
| 2008/0115783 A1 * | 5/2008 | Brain | A61M 16/0488 |
| | | | 128/207.14 |
| 2013/0324798 A1 * | 12/2013 | Molnar | A61M 16/042 |
| | | | 128/200.26 |
| 2019/0054266 A1 * | 2/2019 | Sun | A61M 16/0447 |
| 2019/0059710 A1 * | 2/2019 | Molnar | A61B 1/2676 |

* cited by examiner

VISUAL LARYNGEAL MASK

CROSS-REFERENCE TO RELATED APPLICATION

This is a continuation application of U.S. patent application Ser. No. 16/467,039, filed on Jun. 5, 2019, now granted. The prior U.S. patent application Ser. No. 16/467,039 is a 371 application of the International PCT application serial No. PCT/CN2018/113157 filed on Oct. 31, 2018, which claims the priority benefits of China Application No. 201810124111.1 filed on Feb. 7, 2018 and China Application No. 201821088839.5, filed on Jul. 10, 2018. The entirety of each of the above-mentioned patent application is incorporated herein by reference and made a part of this specification.

BACKGROUND

Technical Field

The present invention belongs to the field of medical instruments, and more specifically, to an improved visual laryngeal mask.

Description of Related Art

The visual laryngeal mask is a system of endotracheal intubation technology and airway management. The biggest feature of the visual laryngeal mask is that a visual system is additionally provided for an existing common laryngeal mask, so that a laryngeal mask can be observed and monitored in real time during and after insertion as well as the a tracheal intubation, thereby making the laryngeal mask more user-friendly, improving the success rate of the intubation, and making patients less exposed to hypoxia, airway damage, and other risks in intubation.

Figure 7:
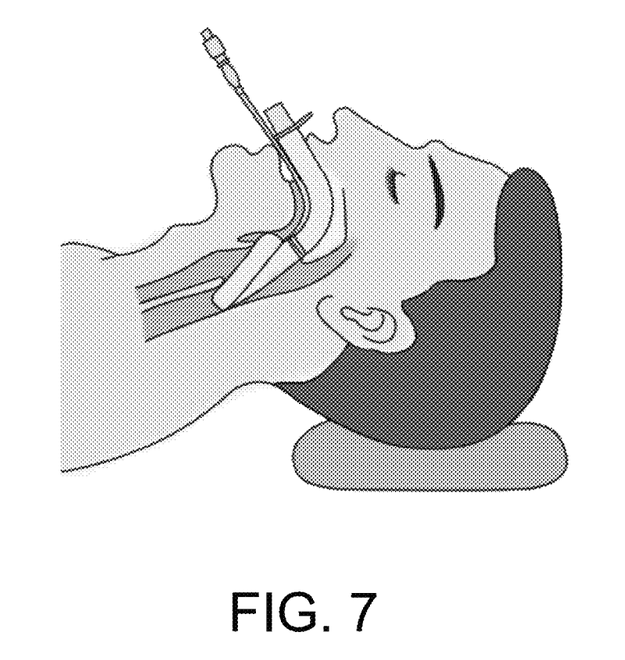
FIG. 7 is a diagram of a state in which a laryngeal mask airbag is inserted into the human throat tissue.

In the course of development, laryngeal masks are divided into common laryngeal masks (first-generation laryngeal masks), intubating laryngeal masks (second-generation laryngeal masks) and double tube laryngeal masks (third-generation laryngeal masks). FIG. 7 is a schematic view showing a state in which the laryngeal mask airbag is inserted into a human throat tissue; the first and second-generation laryngeal masks have the advantages of simple use, rapid establishment of an airway, a high success rate of placement, reliable ventilation, no damage to the throat and tracheal mucosa, but also have drawbacks such as incomplete sealing, an increase of oral secretions, an inability to effectively isolate the respiratory tract and digestive tract, and an initiation of aspiration or reflux, which limits clinical applications. With the development of materials and technologies, the third-generation laryngeal masks are designed as an arc structure based on the advantages of the first and second-generation laryngeal masks, comprising a snorkel and a drainage tube, wherein the drainage tube can enter the gastric tube to achieve gastric drainage, and prevent aspiration and reflux. Meanwhile, its double airbag structure also makes the ventilator and the throat anatomy match closer and seal better. The research practice confirms that the third-generation laryngeal mask has a higher success rate of catheterization, more stable hemodynamics, less drug consumption during the induction period, and fewer complications, and it is widely used in clinical practice. In recent years, with the advances of materials and technologies, a variety of improved third-generation laryngeal masks have appeared, such as Tuoren's double tube laryngeal masks and Jinerkang's Splendid laryngeal masks. Further, for example, Chinese Patent Application No. CN201180042730.2 discloses a laryngeal mask airway device, comprising an airway tube extending from a proximal end to a distal end and leading to an interior of a cover portion at an distal end; the cover portion comprises a back plate and a cuff, the cover portion being shaped to seal around a periphery of an throat inlet without piercing an interior of the throat, wherein the device comprises a guiding device located within the interior of the cover portion and is suitable for directing the drug delivery catheter to the larynx when the laryngeal mask airway device is used with a drug delivery catheter.

The existing visual laryngeal masks have a poor viewing effect, such as the Ctrach system of a conventional visual laryngeal mask, and, for example, the applicant's patent application No. CN206167560 discloses a visual laryngeal mask, comprising a hollow snorkel and an airbag, wherein a camera is provided on an inner wall of an extending end of the ventilating cavity at a position near the airbag, and a cleaning channel is provided on one side of the camera for rinsing the debris on the camera during an operation; wherein the camera and an opening of the airway of the visual laryngeal mask are basically flush. In actual operation, when a product is inserted into a throat, the epiglottis will block the region around the exit of the airway, and meanwhile, the camera will be invisibly blocked and unable to see the glottis. The observation will fail and cannot realize visualization in a real sense. Meanwhile, the cleaning channel faces toward the camera, and it is difficult to completely clean the debris of the camera. How to use a camera to achieve the best visual effect, and at the same time design a structure more in line with a human throat structure, so as not to increase a patient's treatment pain so as to ensure the use of intubation, has become a recognized problem.

SUMMARY

In order to solve the problem that the visible visual mask of the prior art has a poor visual effect, and the structural design is rough and the physiological structure is not highly adapted, the present invention provides an improved visual laryngeal mask comprising a snorkel, an end of which is provided with a fixing seat, wherein the fixing seat is provided with an airbag, and the fixing seat has a recess which is provided with an airway opening; an inner wall of the snorkel longitudinally extends an imaging cavity, wherein the imaging cavity has a built-in imaging device, and the imaging cavity and a cleaning channel protrude forward relative to the airway opening to form a stopper which prevents an epiglottis from blocking the imaging device.

Preferably, the inner wall of the snorkel longitudinally further extends an imaging cavity, the cleaning channel is provided with a cleaning nozzle facing toward the imaging device.

Preferably, the stopper protrudes from the airway opening by 1-10 mm, and an end of the stopper is concaved to form a recess, and an opening of the imaging cavity is located at a low point of the recess so that a periphery of the opening of the imaging cavity constitutes a rib.

Preferably, the cleaning channel is independently spaced apart from the imaging cavity, and an end of the cleaning channel is bent by 30°~90° toward the imaging device to form a cleaning nozzle for flushing the imaging device.

Preferably, the stopper protrudes from the airway opening by 3 ~5 mm.

Preferably, the end of the cleaning channel is longitudinally provided with at least two rows of cleaning nozzles, each row of cleaning nozzles comprising a vertical cleaning nozzle and a tilt cleaning nozzle facing toward the imaging device, wherein the vertical cleaning nozzle is substantially flush with the imaging device while the tilt cleaning nozzle is located on a front side of the imaging device, with a corner of the cleaning channel being 50°~75°.

Preferably, the stopper comprises a main body portion having a cylindrical outer surface, and a front end portion comprising a first circular arc surface and a second circular arc surface, wherein the first circular arc surface and the second circular arc surface form an arc intersection where a transition is formed.

Preferably, the imaging device is a camera, which protrudes slightly from the opening of the imaging cavity or is flush with the opening of the imaging cavity; and an end of the camera is provided with a light source.

Preferably, the stopper is located in a recess of the fixing seat.

Preferably, the end of the camera is further provided with an LED light, and the camera is closed with a transparent material.

The visual laryngeal mask provided in the present invention has a camera provided in a position where the camera protrudes from the airway outlet, and the camera is concaved, so that the stopper can prevent the epiglottis tissue from obscuring a field of view of the camera to make the field of view clear. A cleaning hole is designed to be perpendicular or inclined to the cleaning channel, and a cleaning agent can completely cover the position of the camera that needs to be cleaned, so that the visual effect is optimized. The stopper provided in the present invention has a cylindrical outer peripheral surface and the ends are all arc transitions which are well adapted to the anatomy of a human throat and do not scratch a physiological tissue.

Another objective of the present invention is to provide a visual laryngeal mask system comprising the above-mentioned visual laryngeal mask and a display device thereof.

The present invention improves the airbag of the laryngeal mask on the basis of the above-mentioned laryngeal mask, and provides a double airbag medical laryngeal mask comprising a snorkel, a distal end of which is provided with a fixing seat, wherein the fixing seat is coated with an airbag and has a back plate, the airbag has a back side, a ventral side and two side walls, and the back side of the airbag is provided corresponding to the back plate of the fixing seat, characterized in that the airbag has an esophagus sealing capsule and an airway sealing capsule, wherein the esophagus sealing capsule is located on a front side of the airway sealing capsule, the esophagus sealing capsule and the airway sealing capsule are in communication and form a separation region between their back sides, so that when the airbag is inflated, an expansion height of the esophagus sealing capsule is smaller than that of the airway sealing capsule; and a separation region corresponds to a boundary between the esophagus and the airway.

Preferably, a front side of the back plate of the fixing seat is sealed with a corresponding back side of the airbag, thereby forming a separation region between the esophagus sealing capsule and the airway sealing capsule, and the two sides of the esophagus sealing capsule and the airway sealing capsule remain connected.

Preferably, the front side of the back plate of the fixing seat is bonded or thermally joined to the corresponding back side of the airbag.

Preferably, the back side of the airbag is provided above the back plate, and the back side of the airbag has a median capsule body and an outer side capsule body integrally formed with the median capsule body; the median capsule body is adapted to a shape of the back plate and in contact with the back plate, and a connection region is formed between a front side of the median capsule and the front side of the back plate so as to form a separation region between the esophagus sealing capsule and the airway sealing capsule.

Preferably, the airbag is roughly in a shape of an oval ring, and the two side walls of the airbag form an arc transition at their respective boundary regions.

Preferably, a transverse dimension of the esophagus sealing capsule is gradually reduced from a rear side to the front side.

Preferably, the arc transition portion has an accurate transition to provide a smooth transition of the side walls of the airbag.

The double airbag laryngeal mask provided in the present invention has an expansion height of the back side of the esophagus sealing capsule less than that of a back side of the airway sealing capsule when inflated; while the same function with the existing airbag (the airway sealing capsule is used for sealing the airway) is achieved, the esophagus sealing capsule with a small expansion volume seals the esophagus, which prevents gas from leaking into the esophagus (causing poor ventilation and bloating) and prevents gastric juice from returning to the airway, thereby causing an airway infection and poor ventilation; meanwhile, it can reduce pressure on the esophagus; because the laryngeal mask is strong against the throat tissue, it is better to reduce the damage.

Because of the occurrence of air leaks and reflux of gastric juice during the establishment of artificial airways, although the third-generation laryngeal masks have a drainage function, the operation is complicated, and it is difficult to detect the occurrence at any time or when the situation is critical. The sealed esophageal capsule provided in the present invention directly seals the esophagus and prevents gas from leaking into the esophagus when an airbag enters the throat.

DESCRIPTION OF THE EMBODIMENTS

The present invention will be described in detail below with reference to the accompanying drawings. It should be understood that:

In the description of the present invention, the shapes of "tongue" and "oval ring", and the modifier "roughly" before the shapes are used to describe the shape of a structure of the present invention, but do not necessarily mean that the structure must be strictly in the shape. Instead, the shapes are allowed to have a suitable geometric adjustment or deformation. Some deviations or deformations from the standard shapes also fall within the scope of the present invention, and the structure provided in the present invention is not strictly in a certain shape. The descriptions of some shapes which are intended to facilitate the understanding of those skilled in the art are not to be construed as limiting the scope of the present invention. All shapes achieving the intended aims of the present invention fall within the protection scope of the present invention.

In the description of the present invention, the "back side", "ventral side", "front side" and "rear side" indicate positional relationships based on the positional relationship shown in the drawings, and are merely for easy and simplified description of the present invention. It is not intended or implied that the structures and parts referred to must have a particular orientation, are constructed and operated in a particular orientation, and thus are not to be construed as limiting the present invention.

Embodiment 1: Improved Visual Laryngeal Mask

Figure 1:
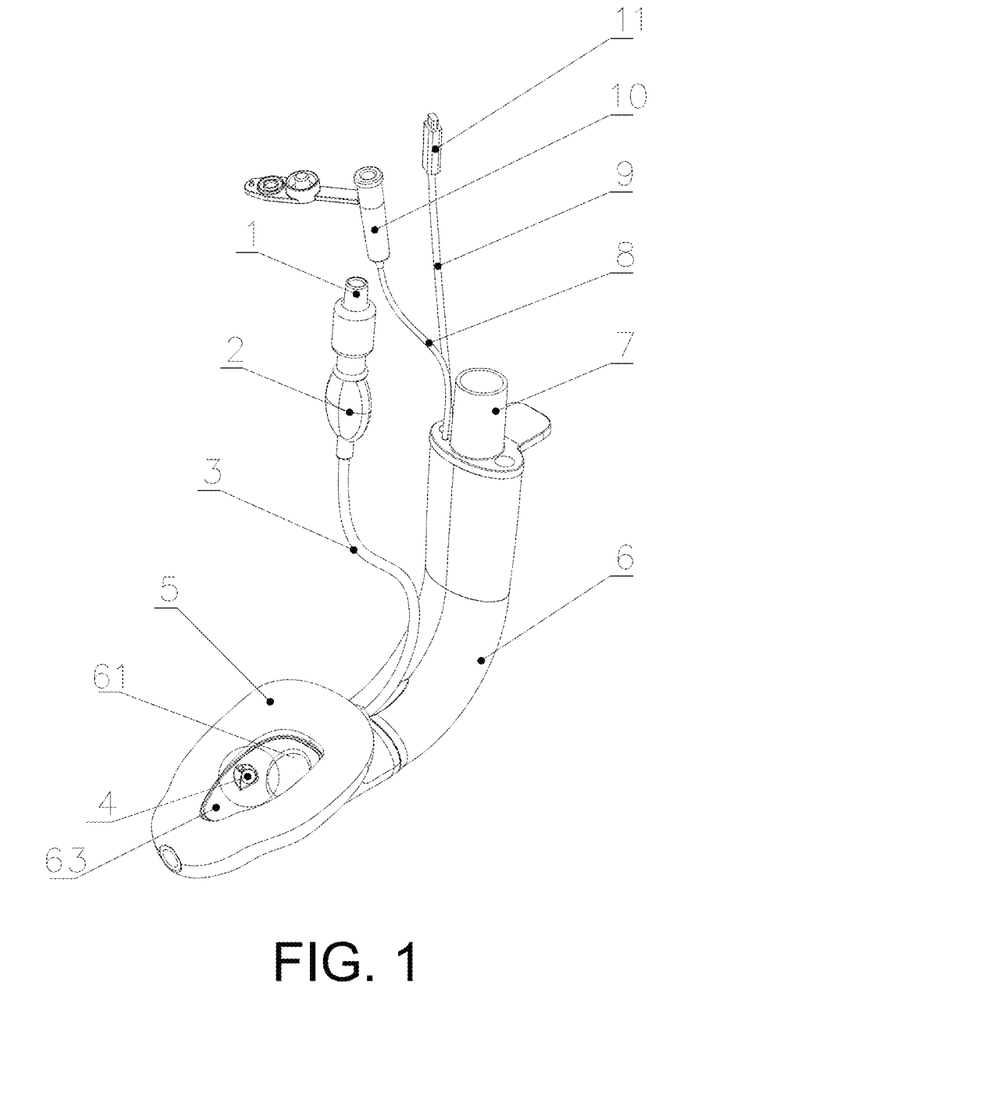
FIG. 1 is a structural diagram of a visual laryngeal mask provided in the present invention.

As shown in FIG. 1, the laryngeal mask comprises a snorkel (tube) 6, wherein an insertion end portion of the snorkel 6 is provided with an airbag 5 which is roughly in the shape of an oval ring and fixed to the fixing seat 63 formed at an end of the snorkel 6. The fixing seat 63 has a recess which is provided with an airway opening 61. The snorkel 6 enters the airway through the airway opening, and an inner wall of the snorkel longitudinally extends an imaging cavity and a cleaning channel, wherein the imaging cavity has a built-in camera 4, and the imaging channel and the airway opening of the cleaning channel continues to extend forward, where a convex stopper 62 is integrally formed, that is, the stopper 62 is convex relative to a plane of the airway opening on the fixing seat, so that the stopper 62 can push and block physiological tissue into other regions to prevent an epiglottis from blocking the camera 4. A peripheral portion of an opening of the imaging cavity and an end of the cleaning channel constitutes a front end portion 621 of the stopper 62, wherein the front end portion 621 is concavely recessed toward the opening direction of the imaging cavity, so that an opening end of the imaging cavity is located at a low point of the recess, and the peripheral portion of the opening of the imaging cavity (which may also be said to be the peripheral portion of an end of the stopper) constitutes a function similar to a rib, the rib blocking the physiological tissue into other regions than the stopper; preferably, the inventors of the present invention find that when the stopper 62 protrudes from the airway opening 61 by 1-10 mm, that is, the stopper 62 is convex relative to a plane of a periphery of the airway opening, but the stopper is still in the recess of the airbag fixing seat 63, which achieves an optimal visual effect while preventing the epiglottis from blocking the camera. As an optimal implementation manner, according to the adult glottal size of about 21±4 mm, the tracheal size is about 17±2 mm; according to the relative positional relationship between the glottis and the laryngeal mask during the use of the laryngeal mask, the range of the camera observation to be observed is preliminarily determined to make the images their clearest; through an analysis of a glottal size and a laryngeal mask size, combined with the positional relationship of the laryngeal mask and the glottis, an image acquisition direction of the camera is determined. When the stopper 62 protrudes from the airway opening 61 by 3-5 mm, a clear and complete glottis can be seen.

Figure 3:
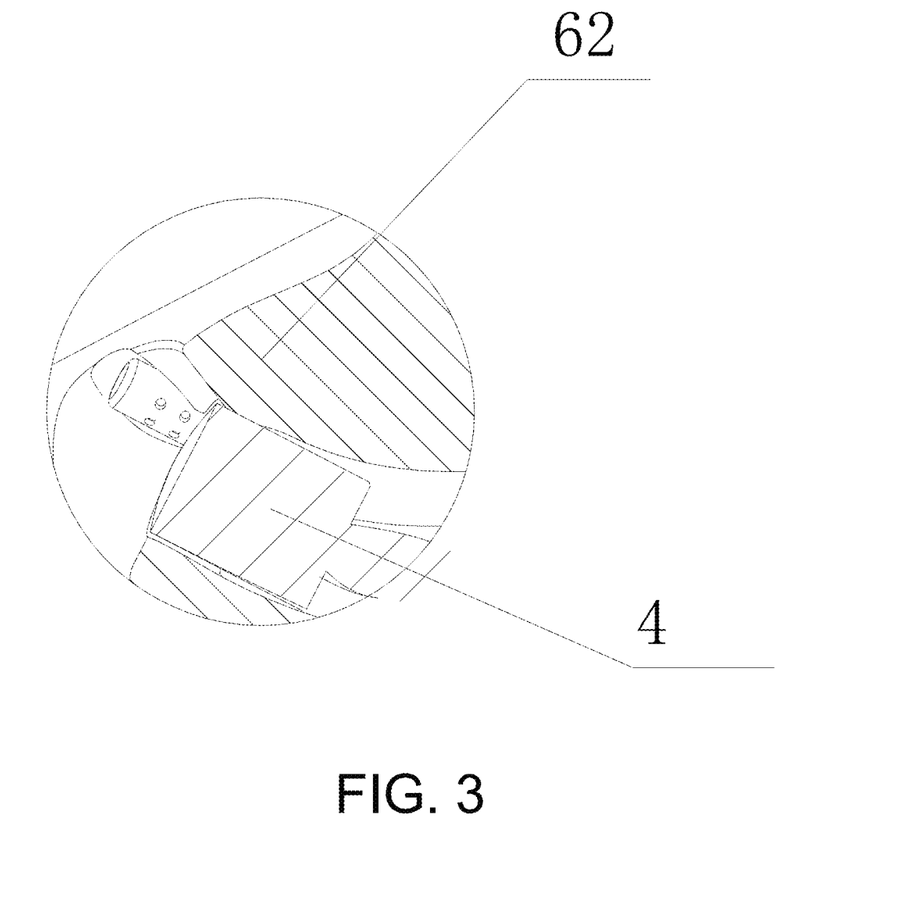
FIG. 3 is a structural diagram of a stopper provided in the present invention.

Wherein, as shown in FIG. 3, the camera 4 may protrude slightly from the opening of the imaging cavity, and may be flush with the opening end of the imaging cavity, but still at the low point of the recess of the stopper, and a shape of the stopper may be varied. For example, the whole stopper has the shape of a shrunken ball; in this case, the stopper in the shape of a shrunken ball has a smooth contour and no sharp edges. Compared with a triangle or other stoppers with sharp sides, the stopper will not make a patient uncomfortable during an operation. For another example, the stopper is divided into a longitudinally extending main body portion 622 in a cylindrical shape, and the front end portion 621, wherein a part of a side wall of the cylindrical main body portion is integrally coupled with a wall surface of the laryngeal mask (because the stopper itself is an imaging cavity extending from the side wall of the snorkel), and a side wall surface adjacent to the airway opening is cylindrical. The front end portion comprises a first semi-circular surface 6211 and a second semi-circular surface 6212 which are integrally connected, and the first semicircular surface 6211 and the second semicircular surface 6212 are not flat surfaces, each having a gradually concave arc surface. An intersection of the first semi-circular surface 6211 and the second semi-circular surface 6212 is an arc transition, and the transition of the intersection has a transition 6213, that is, the first semi-circular surface 6211 and the second semi-circular surface 6212 have an included angle, for example, approximately 90°, so a depth of the recess is deepest at the transition 6213 of the intersection, and a circular transition of the intersection is also provided between the second semi-circular surface and a front side portion of the recess of the fixing seat 63. The development of the structure fits the anatomy of the human throat better, which does not cause a discomfort and facilitates the popularization of the visual mask. Most importantly, due to the physiological characteristics of the epiglottis tissue, the stopper of the structure and the flange (rib) formed at the periphery may cause the epiglottis to be squeezed to the side or block the path of the epiglottis tissue, thereby eliminating the defect of the original patent application Publication No. CN 206167560U where the visual field of the visual device is blocked; being at the low point of the recess, the camera is not easily smeared, thereby effectively reducing cleaning frequency.

Figure 2:
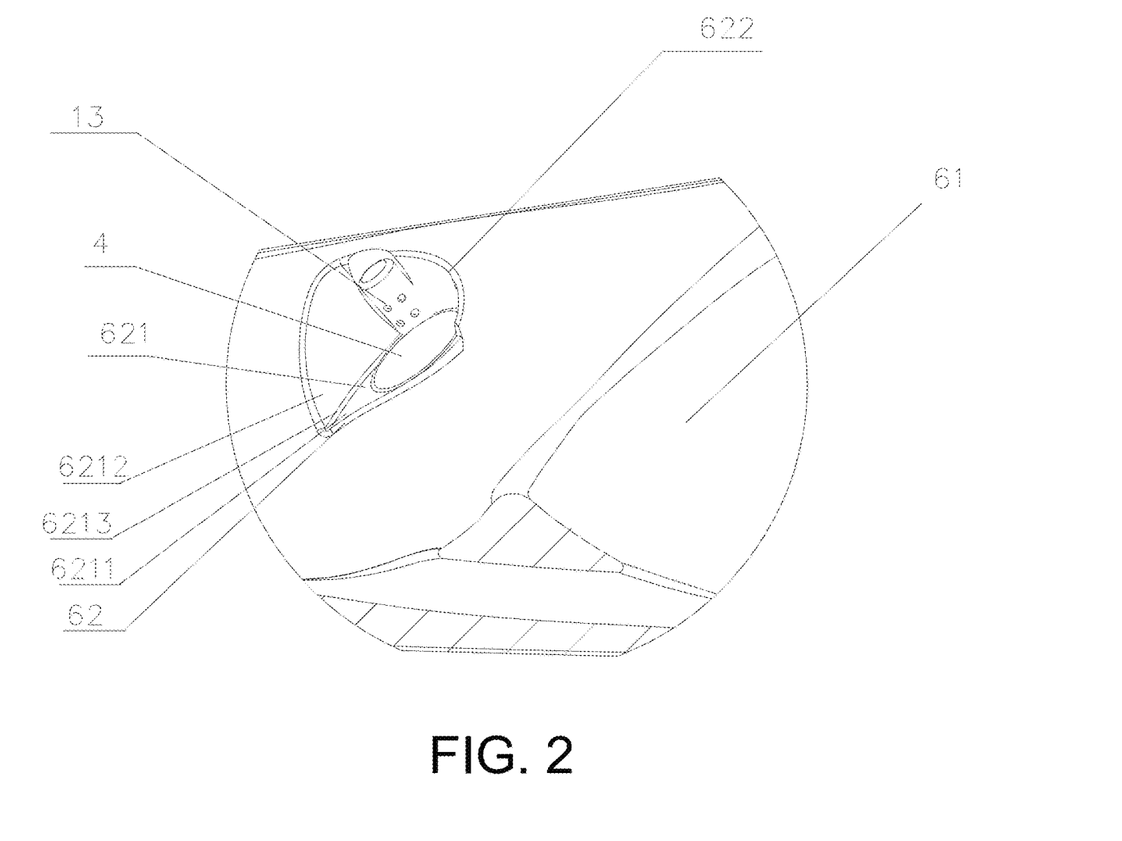
FIG. 2 is a diagram of an insertion end of the visual laryngeal mask provided in the present invention.

In addition, as shown in FIG. 2, the cleaning channel is provided with a cleaning nozzle 13 facing toward the camera. In order to ensure that the cleaning nozzle 13 is opposite to the camera 4, the cleaning nozzle 13 is slightly higher than the camera 4 or flush with the camera 4, the cleaning nozzle is aligned with the camera to spray a cleaning agent.

In addition, a front end of the camera is equipped with an LED light, and the camera is fixed in the imaging cavity in various ways which include, but are not limited to, bonding, screwing or clamping, and the opening end of the imaging cavity is closed with a transparent material. The airbag 5 is connected with an inflation tube 3, an indicative balloon 2 and an inflation valve 1. A front end of the snorkel 6 is provided with a connector 7, the camera is connected with a data line 9 and a data connector 11, the data connector and the display device are connected to form a visual laryngeal mask system, and the cleaning channel is connected with a tensing tube 8 and a tensing fitting 10. The airbag 5 is filled with gas through the inflation valve 1 to form a seal around a patient's airway opening, and the protruding stopper 62 can prevent the epiglottis from obstructing the field of view of the camera.

Embodiment 2: Improved Visual Laryngeal Mask

Figure 4:
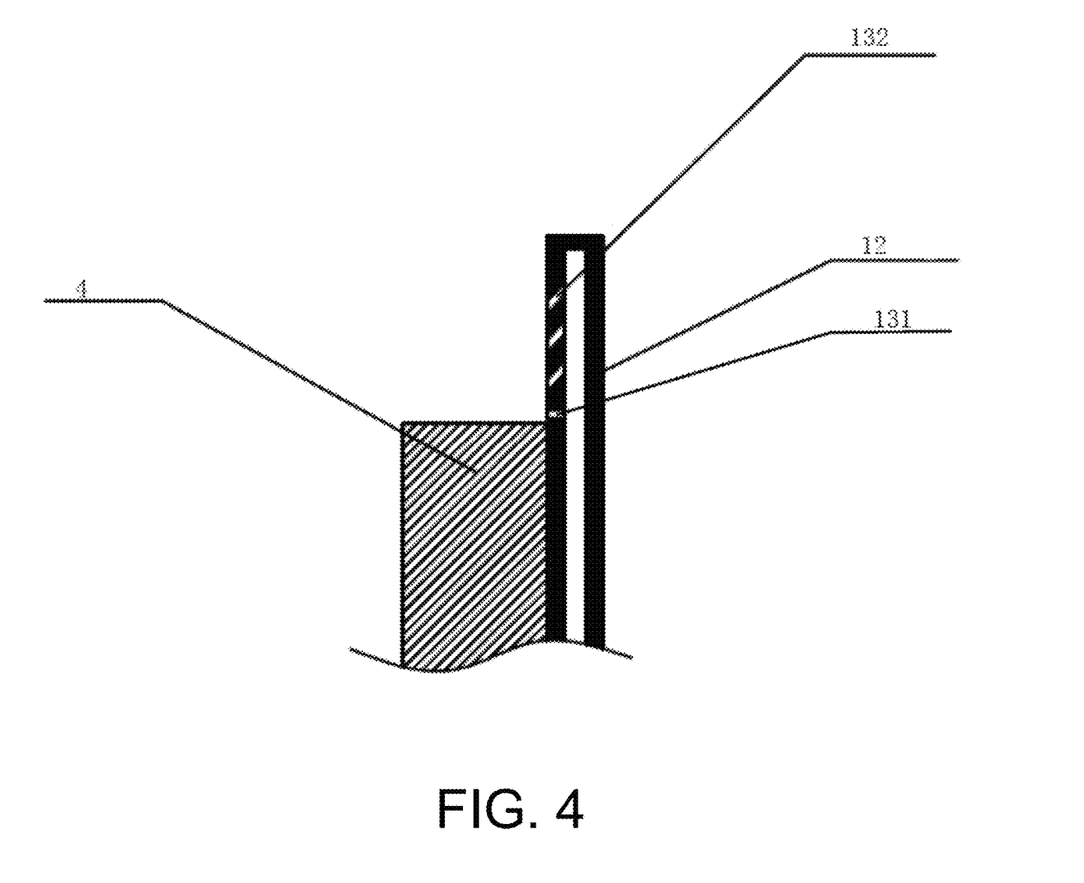
FIG. 4 is a cross-sectional view of an imaging device and a cleaning channel provided in the present invention.

As shown in FIG. 4, the visual laryngeal mask provided in the present invention has at least two rows of cleaning nozzles facing toward the camera in the longitudinal direction of the cleaning channel 12. The position of the cleaning nozzle relative to the camera has an important influence on the cleaning effect; for example, cleaning nozzles in former applications are all vertical cleaning nozzles, that is, an included angle between the cleaning nozzles and the cleaning channel or the imaging cavity is 90°, which makes it difficult to clean the device. The inventors of the present invention have found that when, among the two rows of cleaning nozzles, each row of cleaning nozzles consists of a vertical cleaning nozzle 131 which is substantially flush with the camera, and three longitudinally-arranged tilt cleaning nozzles 132 which protrude slightly from the camera (see FIG. 4), the cleaning effect is significantly improved. Preferably, in a specific embodiment of the present invention, the angle between the tilt cleaning nozzle 132 and the cleaning channel 12 is 50°~75°, that is, a small channel formed by bending the end of the cleaning channel 12 by 50°~75° and communicating with the imaging cavity constitutes the tilt cleaning nozzle 132. In this case, the vertical cleaning nozzle 132 and the tilt cleaning nozzle 132 are jointly responsible for the debris on a side wall and a front surface of the camera 4, and the debris on the camera can be completely removed, so as to avoid incomplete cleaning when the original design of the cleaning nozzles is adopted.

Field of view of the visual laryngeal mask provided in the present invention

Figure 5:
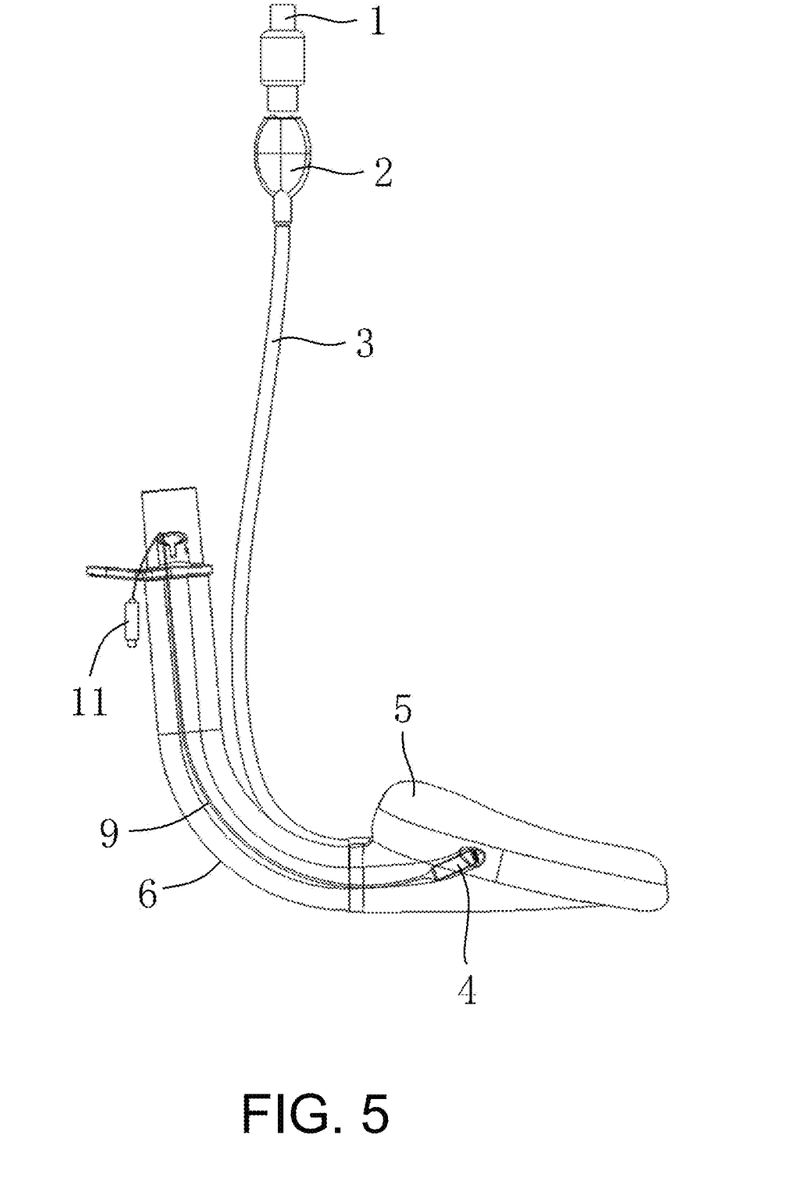
FIGS. 5-6 are diagrams of the field of view of the visual laryngeal mask provided in the present invention.
Figure 6:
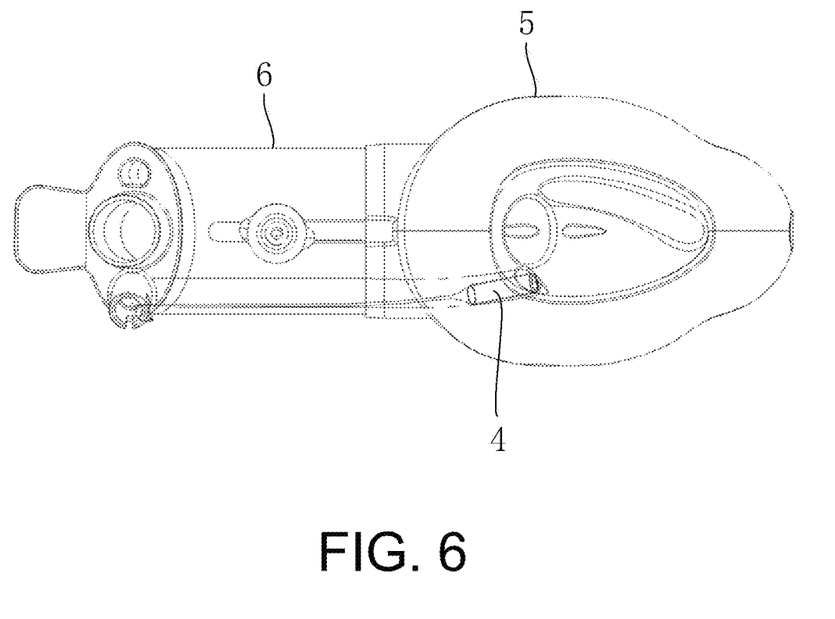

In order to better understand how to determine the position of the protrusion, and how to achieve an optimal field of view, the present invention mainly explores the influence of the positional relationship of the camera relative to the laryngeal mask on an overall visual effect of the visual laryngeal mask. Through a functional analysis in the process of clinical use, the mathematical method is used to find the best position for observation, specifically in the following steps:

1) According to the relative positional relationship between the glottis and the laryngeal mask, determining the range of the glottis image to be observed, and the glottal position should be observed as much as possible in the visual system of the laryngeal mask based on the adult glottal size of 21±4 mm and the trachea size of about 17±2 mm; according to the relative positional relationship between the glottis and the laryngeal mask during use of the laryngeal mask, as shown in FIG. 4 and FIG. 5, preliminarily determining that the image in the range that the camera should observe should be the clearest; through an analysis of the glottal size and the laryngeal mask size, combined with the related positional relationship of the laryngeal mask and the glottis, determining the image acquisition direction of the camera, so that the visual system can see the most complete and clearest glottis through this direction.

2) Finding the spatial coordinates of the imaging end of the camera relative to the iconic structure of the laryngeal mask. According to the acquisition direction of the camera obtained in step 1), preliminarily determining the central position of the imaging end of the camera by reversing the position of the position; according to the size of a common camera, preliminarily determining the positional relationship between the installing position of the camera and the laryngeal mask itself, and finally obtaining the following expression, combined with a relevant mathematical analysis.

Ending position of the camera (central point coordinate A):

$$x_1 = (r+R+l_2)\cos\theta$$

$$y_2 = 0$$

$$z_1 = (r+l_1)\sin\theta$$

Starting position of the camera (central point coordinate B):

$$x_2 = -l_2 \cos\alpha(\cos\beta + \cos\gamma)$$

$$y_2 = -l_2 \cos\beta(\cos\alpha + \cos\gamma)$$

$$z_2 = -l_2 \cos\gamma(\cos\beta + \cos\alpha)$$

Taking the central position of the airway exit as the coordinate origin, the vertical air channel exit end axis is the Y axis, the horizontal direction is the X axis, and the vertical direction is the Z axis (as shown in the following figures).

Point A is the central point of the end point of the camera, and the coordinates are (x1, y1 and z1).

r: radius of the observation channel

R: radius of the airway of the snorkel $l_2$: the shortest distance between the observation channel and the edge of the airway; usually>2 mm °: the included angle between the central line of the camera and the coordinate plane X-Y β: the included angle between the central line of the camera and the coordinate plane Y-Z γ: the included angle between the central line of the camera and the coordinate plane Z-X $l_2$: positioning length of the camera, and the length of the rigid section of the camera 3) Calculating the space coordinates of the camera terminal to determine the relative positional relationship between the camera system and the laryngeal mask.

According to the size of the common camera, preliminarily determining the camera insertion channel trajectory and size, and finally obtaining the following parameter table 1, combined with the relevant mathematical analysis.

TABLE 1

| | Coordinates of observation channel curve Coordinate points (mm) | | |
|---|---|---|---|
| No. | X | Y | Z |
| 1 | 0 | 0 | 0 |
| 2 | 3 | 0 | 0 |
| 3 | 6 | 0 | 0 |
| 4 | 9 | 0.05 | 0 |
| 5 | 12 | 0.1 | 0 |
| 6 | 15 | 0.1 | −0.1 |

TABLE 1-continued

Coordinates of observation channel curve
Coordinate points (mm)

| No. | X | Y | Z |
| --- | --- | --- | --- |
| 7 | 20 | 0.3 | −0.2 |
| 8 | 21 | 0.35 | −0.3 |
| 9 | 22 | 0.45 | −0.4 |
| 10 | 26 | 0.5 | −1 |
| 11 | 29 | 0.7 | −1.5 |
| 12 | 32 | 1.3 | −2.3 |
| 13 | 35 | 2 | −3.8 |
| 14 | 37 | 2.7 | −5 |

The center of the observation channel of the laryngeal mask at the connection between the snorkel of the laryngeal mask and the middle part of the balloon is taken as the origin, and the three-dimensional space curve traced by the above point is the trajectory curve of the laryngeal mask observation channel.

The results show that the laryngeal mask provides the best field of view.

Embodiment 3

Figure 8:
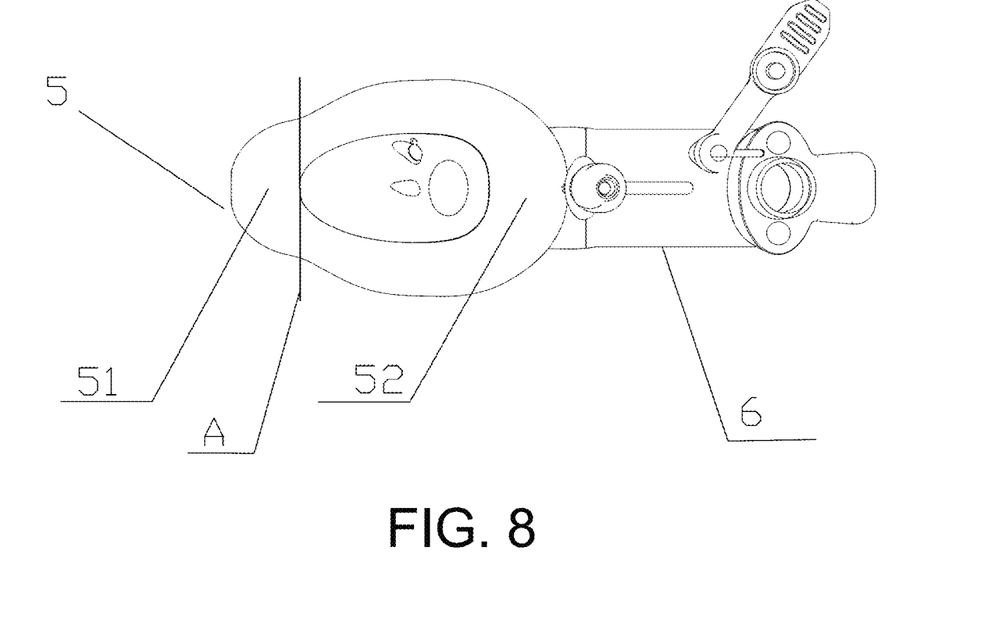
FIG. 8 is a top view of a double airbag medical laryngeal mask provided in the present invention.
Figure 9:
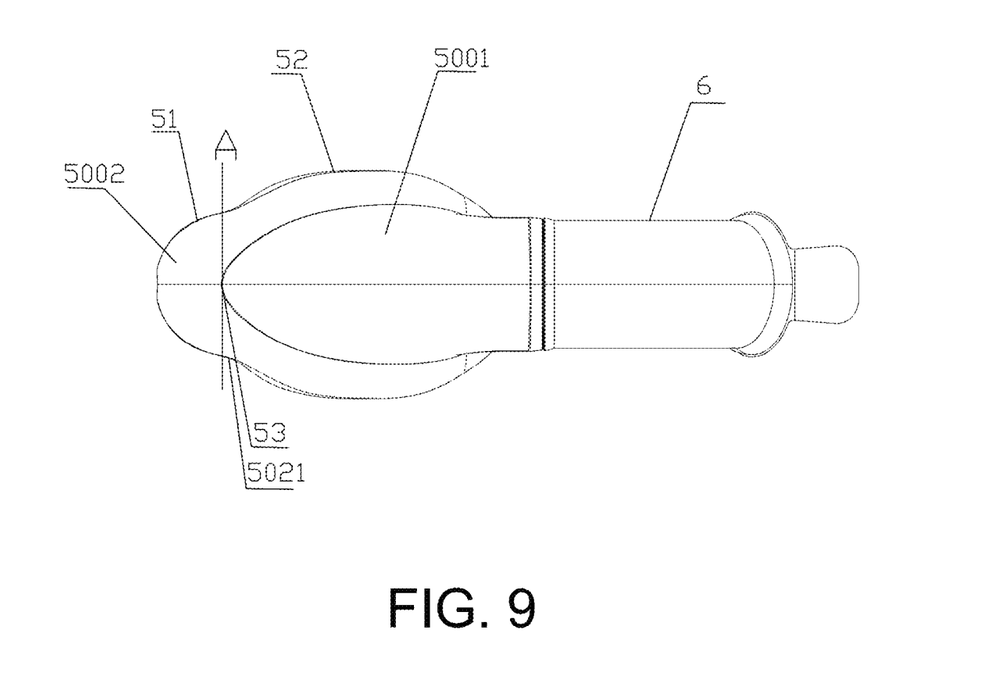
FIG. 9 is a bottom view of the double airbag medical laryngeal mask provided in the present invention.
Figure 10:
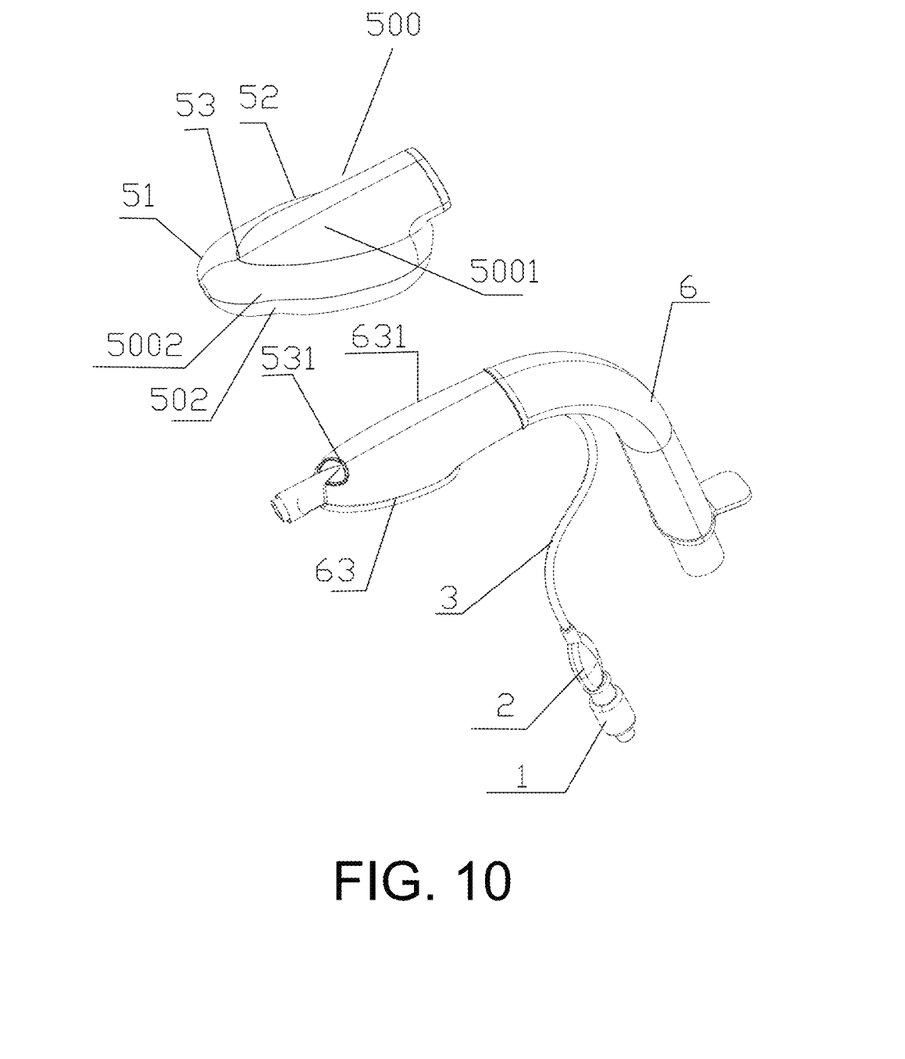
FIG. 10 is a diagram of the disassembly of the double airbag medical laryngeal mask provided in the present invention (separating a fixing seat from the airbag)
Figure 11:
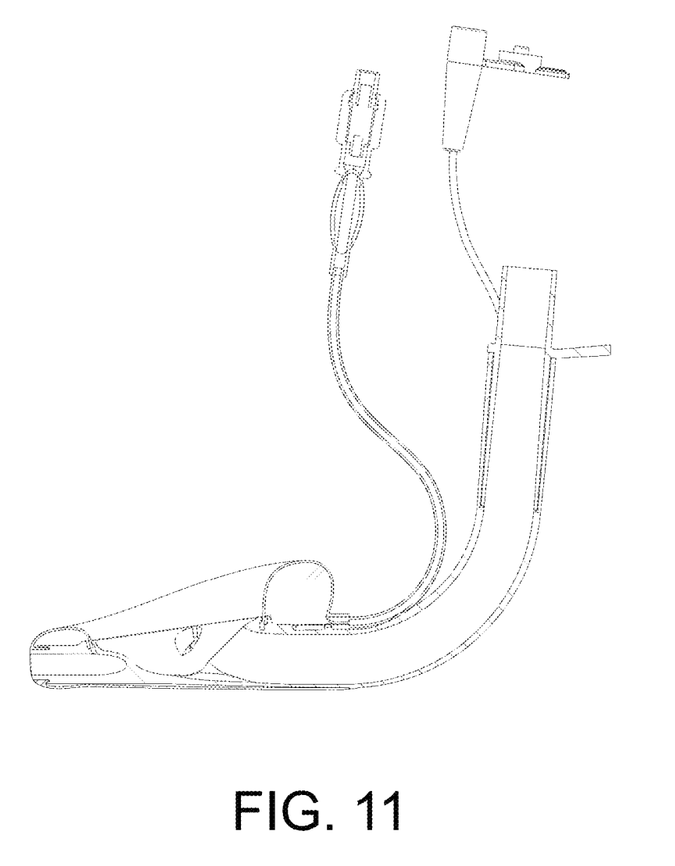
FIG. 11 is a cross-sectional diagram of the double airbag medical laryngeal mask provided in the present invention when not inflated.
Figure 12:
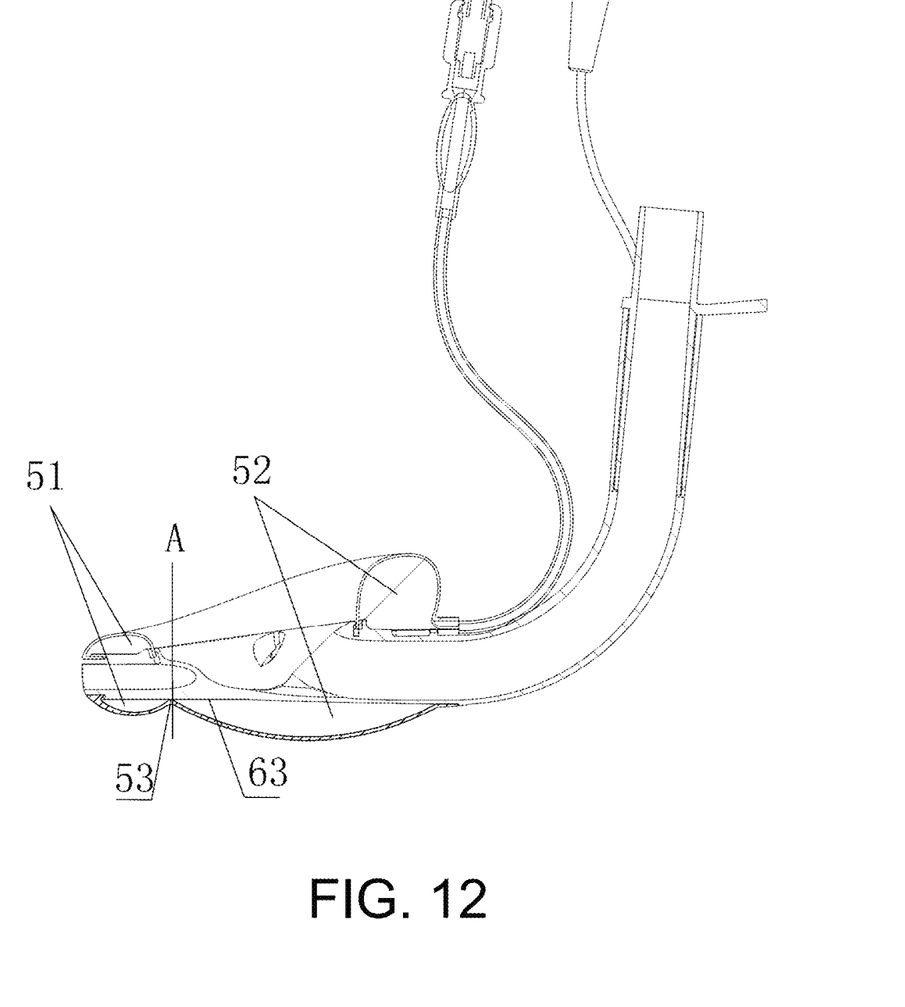
FIG. 12 is a cross-sectional diagram of the double airbag medical laryngeal mask when inflated according to the present invention.

In a preferred embodiment of the present invention, the present invention provides a double balloon medical laryngeal mask, and as shown in FIGS. 8-10, the airbag 5 is used in a double tube laryngeal mask. The laryngeal mask comprises a snorkel 6 and a fixing seat 63 at a distal end of the snorkel and integrally formed with the snorkel 6, the fixing seat 63 comprises a back plate 631, and the airbag 5 is connected to an inflation tube 3, an indicative balloon 2 and the inflation valve 1. The indicative balloon 2 is coated on the fixing seat 63 provided at the distal end of the snorkel 6 of the laryngeal mask, wherein the fixing seat 63 has a back plate 631. Referring to FIG. 10, the airbag 5 has a back side 500, a ventral side (the back side is the ventral side), and two side walls 502, the back side 500 of the airbag being provided correspondingly above and below the back plate 631 of the fixing seat 63. The airbag has an esophagus sealing capsule 51 and an airway sealing capsule 52, and in the present invention, for convenience of understanding, referring to FIGS. 8, 9, and 12, the inventors define a boundary line A, wherein a front side of the boundary line A is the esophagus sealing capsule 51, a rear side of the boundary line is the airway sealing capsule 52, the esophagus sealing capsule 51 being located in a front side of the airway sealing capsule 52. In order to ensure that the gas stays in the esophagus sealing capsule and the airway sealing capsule, the esophagus sealing capsule 51 is still in communication with the airway sealing capsule 52. However, in order to prevent the gas filling efficiency, a separation region 53 is formed between the esophagus sealing capsule 51 and a back side of the airway sealing capsule 52, and through the separation region 53, when the gas in the airway sealing capsule flows toward the esophagus sealing capsule, it can only enter through a non-separation region, that is, a near-by side. Referring to FIG. 12, after inflation, an expansion height of the back side of the esophagus sealing capsule is significantly smaller than an inflation height of the airway sealing capsule, that is, the degree of inflation of the esophagus sealing capsule is smaller than the inflation degree of the airway sealing capsule. The separation region 53 corresponds to a boundary between the esophagus and the airway, and when the airbag is inserted into a throat, the airway sealing capsule 52 is used to seal the airway, and the esophagus sealing capsule 51 is used to seal the esophagus, thereby preventing the gas from leaking into the esophagus (causing poor ventilation and bloating), and preventing returning gastric juice from entering the airway to cause an airway infection and poor ventilation.

A separation region is formed between the esophagus sealing capsule 51 and the back side of the airway sealing balloon 52, and the form of implementation may be various. In a preferred embodiment of the present invention, a front side of the back plate 631 of the fixing seat 63 is connected to the corresponding balloon back side 500 thereof, thereby achieving separation between the esophagus sealing capsule and the region of a back side of the airway sealing capsule, to form a separation region 53, and in addition to this separation region 53. Other than the separation region, other regions remain in communication, including other regions on the back side and two side walls 502. Preferably, the front side of the back plate of the fixing seat and its corresponding back side of the airbag may be bonded or thermally joined. In this embodiment, the front side of the back plate of the fixing seat is bonded to the corresponding back side of the airbag in a sealing form;

Specifically, in the present embodiment, as shown in FIG. 10, the back side 500 of the airbag is provided above the back plate 631, and the back side 500 of the airbag has a median capsule 5001 and an outer side capsule 5002 integrated with the median capsule 5001. The molded outer capsule 5002 has a shape in which the median capsule 5001 is adapted to the back plate 631, wherein an inner side of the median capsule is in contact with the back plate 631, the outer side capsule 5002 is surrounded on a circumferential side of the back plate, and a connection region 531 is formed between a front side of the median capsule 5001 and the front side of the back plate 631. The connection region is a bonding region in this embodiment, and can realize a separation between the esophagus sealing capsule and the airway sealing capsule. As shown in FIG. 12, referring to FIG. 11, after inflation by the inflation catheter 2, an expansion height of the rear airway sealing capsule is significantly higher than the expansion height of the front esophagus sealing capsule due to the blocking of the separation region, that is, the communication between the side walls does not completely hinder the inflow of the inflation gas, and the esophagus sealing capsule with a small expansion volume can significantly reduce the pressure on the esophagus; because the laryngeal mask is strong against the throat tissue, it is better to reduce the damage.

The airbag 5 is roughly in the shape of an oval ring, and the two side walls of the balloon form an arc transition 5021 at their respective boundary regions. A lateral dimension of the esophagus sealing capsule 51 is gradually reduced from a rear side to a front side, thereby further reducing the compression against a throat, and the arc transition portion has an arc transition which forms a smooth transition of the side wall of the airbag. The physiological structure is adapted to avoid discomfort.

Although the embodiments disclosed in the subject matter described herein have been particularly shown and described in detail above and in detail in connection with several exemplary embodiments, a plurality of modifications, changes and omissions may be made by those skilled in the art without departing from the teachings, principles and concepts. Accordingly, the proper scope of the disclosed invention is intended to be determined only by the broadest interpretation of the appended claims to cover all of these modifications, changes and omissions.

What is claimed is:

1. An improved visual laryngeal mask, comprising a tube, an end of the tube is provided with a fixing seat, wherein the fixing seat is provided with an airbag, and the fixing seat has a recess which is provided with an airway opening; an imaging cavity extends longitudinally inside an inner wall of the tube, wherein the imaging cavity is able to be used for a built-in imaging device, and the imaging cavity protrudes forward relative to the airway opening to form a stopper which is adapted to prevent an epiglottis from blocking the imaging device; wherein a front end of the stopper is concaved to form a recess, and an opening of the imaging cavity is located at a low point of the recess of the stopper.

2. The improved visual laryngeal mask as claimed in claim 1, wherein a back side of the airbag is provided corresponding to a back plate of the fixing seat; the airbag has an esophagus sealing capsule and an airway sealing capsule, wherein the esophagus sealing capsule is located on a front side of the airway sealing capsule, the esophagus sealing capsule and the airway sealing capsule are in communication and form a separation region between their back sides, so that when the airbag is inflated, an expansion height of the esophagus sealing capsule is smaller than an expansion height of the airway sealing capsule; and the separation region is configured to correspond to a boundary between an esophagus and an airway.

3. The improved visual laryngeal mask as claimed in claim 2, wherein the airbag is generally in a shape of an oval ring, and two side walls of the airbag form an arc transition portion at their respective boundary regions; the arc transition portion has an arc transition to provide a smooth transition of the side walls of the airbag.

4. The improved visual laryngeal mask as claimed in claim 1, wherein the stopper protrudes from the airway opening by 1-10 mm.

5. The improved visual laryngeal mask as claimed in claim 4, wherein the stopper protrudes from the airway opening by 3-5 mm; and the stopper is located in the recess of the fixing seat.

6. The improved visual laryngeal mask as claimed in claim 1, wherein a front side of a back plate of the fixing seat is sealed with a corresponding back side of the airbag, thereby forming a separation region between an esophagus sealing capsule and an airway sealing capsule; and the front side of the back plate of the fixing seat is bonded or thermally joined to the corresponding back side of the airbag.

7. The improved visual laryngeal mask as claimed in claim 6, wherein the back side of the airbag is provided above the back plate, and the back side of the airbag has a median capsule and an outer side capsule integrated with the median capsule; the median capsule is adapted to a shape of the back plate and is in contact with the back plate, and a connection region is formed between a front side of the median capsule and the front side of the back plate so as to form a separation region between the esophagus sealing capsule and the airway sealing capsule.

8. The improved visual laryngeal mask as claimed in claim 1, wherein the stopper comprises a main body portion having a cylindrical outer surface, and a front end portion comprising a first circular arc surface and a second circular arc surface, wherein the first circular arc surface and the second circular arc surface form an arc intersection where a transition is formed.

9. The improved visual laryngeal mask as claimed in claim 1, wherein the imaging device is a camera, which protrudes slightly from an opening of the imaging cavity or is flush with the opening of the imaging cavity; and an end of the camera is provided with a light source.

* * * * *